US009649063B2

(12) United States Patent
Kokko (10) Patent No.: US 9,649,063 B2
(45) Date of Patent: May 16, 2017

(54) POINT OF CARE MEASUREMENT OF PATIENT SENSITIVITY TO ANESTHETICS

(71) Applicant: General Electric Company, Schenectady, NY (US)

(72) Inventor: Pietari Aleksis Kokko, Espoo (FI)

(73) Assignee: General Electric Company, Schenectady, NY (US)

( * ) Notice: Subject to any disclaimer, the term of this patent is extended or adjusted under 35 U.S.C. 154(b) by 536 days.

(21) Appl. No.: 14/107,192

(22) Filed: Dec. 16, 2013

(65) Prior Publication Data

US 2015/0164412 A1    Jun. 18, 2015

(51) Int. Cl.
*A61B 5/04* (2006.01)
*A61B 5/00* (2006.01)
*A61B 5/0476* (2006.01)

(52) U.S. Cl.
CPC .......... *A61B 5/4821* (2013.01); *A61B 5/0476* (2013.01); *A61B 5/4839* (2013.01)

(58) Field of Classification Search
CPC combination set(s) only.
See application file for complete search history.

(56) References Cited

U.S. PATENT DOCUMENTS

2006/0167722 A1* 7/2006 MRF Struys ...... A61B 5/02055
705/3

OTHER PUBLICATIONS

"Navigator 2 Therapy White Paper" Yudkovitch, pp. 1-49.
"On-line estimation of propofol pharmacodynamic parameters", Sartori et al., 2005. pp. 1-5.
"Validaton of remifentanil propofol response surfaces for sedation, surrogates of surgical stimulus, and laryngoscopy in patients undergoing surgery", Johnson et al., Anesthesia and Analgesia 106, 2 (Feb. 2008).
Two-stage vs. mixed-effect approach to pharmacodynamic modeling of propofol in children using state entropy:, Hahn et al., Pediatric Anaesthesia 21, 6 (2011): 691-698.
"Optimizing intravenous drug administration by applying pharmacokinetic/pharmacodynamic concepts", Struys et al, British Journal of Anaesthesia 107(1) 38-47, 2011.

* cited by examiner

*Primary Examiner* — Michael Kahelin
*Assistant Examiner* — Mitchell E Alter
(74) *Attorney, Agent, or Firm* — Andrus Intellectual Property Law LLP (57) ABSTRACT

A method and system for monitoring a patient under anesthesia involves determining a drug sensitivity index for the patient. Patient demographic information and amount of anesthetic information is obtained, wherein the amount of anesthetic information includes each drug administered to the patient and the dose amount thereof. An effect site concentration, which represents a total anesthetic concentration in a patient's brain, is then estimated based on the anesthetic information. An expected response is determined based on the demographic information and the effect site concentration. Physiological data is recorded from sensors mounted to a patient, and a depth of anesthesia is determined based on physiological data. An actual response of the patient is then determined based on the depth of anesthesia and the effect site concentration. Finally, a drug sensitivity index is determined for the patient by comparing the expected response to the actual response.

20 Claims, 5 Drawing Sheets

Hill regression curve fitted to the delayed values.

POINT OF CARE MEASUREMENT OF PATIENT SENSITIVITY TO ANESTHETICS

BACKGROUND

Maintaining appropriate anesthesia during surgical operation is difficult. Clinicians providing anesthesia to a patient have to continuously respond to changes in the patient's condition and, when needed, take emergency actions. One key to managing anesthesia is maintaining an appropriate sedation level for a patient, which requires accurate assessment of a patient's sedation level and an understanding of how that particular patient will respond to the administered anesthetic drugs.

Prior art anesthesia care and monitoring has focused on responsive data—determining a patient's current sedation level as a result of anesthesia that has already been administered. For example, the common indicator for sedation level is depth of anesthesia monitoring, such as State Entropy (SE) or Bispectral Index (BIS). However, depth of anesthesia monitoring only provides responsive data, information about the effect that previously administered anesthesia has already caused. Such monitoring does not provide proactive information regarding the patient's future state. Depth of anesthesia monitoring is important; however, anesthesia care would be significantly improved if clinicians could predict a patient's future state, such as how a patient will respond to administration of an anesthetic drug. It is desirable for clinicians to be able to predict patient response, and to be able to apply that prediction into the monitoring and anesthetic maintenance for patients.

Point of care modeling, which is modeling patient state during operation to aid clinical decision making, is a new and promising information source in anesthetics that aims to provide an indicator for patient sedation level. Population models are available that offer information about average patient responses to anesthetic drugs for a particular demographic or population. Typically effect site concentrations predicted by a drug model are presented in population scale. However, when predicting the sedation level according to population models, the result may not be accurate for a single patient. Population data is not patient-specific and often provides information that varies dramatically from data gathered by depth of anesthesia monitoring. Thus, population models are not a reliable source on which a clinician can depend to predict a patient's drug reaction, and actually have the potential to lead clinicians astray. The difference between the population model results and the depth of anesthesia monitoring can increase cognitive load to clinicians by adding yet another parameter to track.

Accurate anesthetic drug administration, for example during a surgical procedure, is extremely important because incorrect dosing can have large consequences; under dosing may lead to patient waking up during operation and overdosing can cause hemodynamic instability. Further, high sensitivity to anesthetics is a known risk factor when administering anesthesia. Because clinicians are unable to predict in advance what a patient's sensitivity level will be, they cannot predict what the sedation level will be. Since anesthetic drugs may take long time to take effect, clinicians are often stuck trying to react to situations of overdosing or under dosing. Thus, a parameter is needed that allows a clinician to better estimate the risks of anesthesia and to make more informed decisions about courses of anesthesia administration.

SUMMARY

The present inventor recognized that prior art anesthesia monitoring systems and methods could be significantly improved by providing an indicator of the patient's sensitivity to a particular anesthetic course, and recognized that determining the patient's individual sensitivity to a particular anesthetic course would allow safer anesthesia administration. The present inventor recognized that determining a patient's sensitivity to anesthesia would be of great value for assuring that patients are not administered an incorrect dosing that causes their sedation level to become too heavy or too light. For example, providing a sensitivity value for the patient's reaction to a particular anesthetic course may allow a clinician, such as an anesthesiologist or anesthetist, to more accurately dose the patient so that the anesthesia wears off at the proper time and the patient's awareness returns promptly after the conclusion of the operation. Further, recent studies indicate that patients with a high sensitivity to anesthesia have a higher risk of post-operative mortality and often experience slower post-operative recovery. Accordingly, determining a point of care measurement of a patient's sensitivity to anesthesia can provide insight upon which the clinician may optimize anesthesia levels and avoid negative consequences of providing too much anesthetic to a patient. Moreover, in addition to maintaining optimal anesthesia, the patient sensitivity measurement allows the clinician to detect an abnormal response to anesthetics, which may indicate that the patient has an underlying problem that may need identification and or treatment. Likewise, such a measurement may help a clinician identify underlying risk, such as identifying a high-risk patient, and make a more informed decision regarding the anesthetic course that should be delivered.

As disclosed herein, the inventor has discovered that population model information can be correlated with sedation-level monitoring to provide a patient-specific model for sedation level—e.g., a model of a patient's reaction to a particular course of anesthesia, including the patients past, current, and future states from the time of anesthesia administration up to the time of that the anesthesia wears off. The disclosed methods and systems automatically predict the patient sedation level by using drug modeling combined with depth of anesthesia monitoring. By applying the disclosed model, a drug concentration can be expressed as an index of brain activity and vice versa, and the future sedation level and time of return of consciousness for a patient can be estimated.

As disclosed herein, automatic State Entropy (SE) scaling for synergetic effect site concentration (Ce) can provide patient-specific predictive PK/PD models or alternatively a prediction of SE values. In one embodiment, a method of monitoring a patient under anesthesia includes obtaining patient demographic information and amount of anesthetic information, wherein the amount of anesthetic information includes each drug administered to the patient and the dose amount thereof. The method further includes using a processor to estimate an effect site concentration that represents a total anesthetic concentration in the patient's brain, and further to determine an expected response of a patient based on the demographic information and the effect site concentration. Physiological data is recorded from sensors mounted to the patient, from which a depth of anesthesia for the patient is determined based on the physiological data. An actual response of the patient is then determined based on the depth of anesthesia and the effect site concentration. The actual response and the expected response are then compared to determine a drug sensitivity index for the patient.

For example, the physiological information recorded from the patient may be EEG data, and the depth of anesthesia monitoring may be based on entropy determination. The expected response and the actual response may each be half-maximal effective concentration ($EC_{50}$) values—e.g., the effect site concentration when the entropy is 50 ($SE_{50}$ value). In such an embodiment, the drug sensitivity index may be expressed as a ratio between the expected response $EC_{50}$ value and the actual response $EC_{50}$ value. The effect site concentration may be determined using a drug modeling method, such as a pharmacokinetic model normalized to a corresponding pharmacodynamic model (a PK/PD model).

A monitoring system for monitoring a patient under anesthesia includes a depth of anesthesia monitor that records physiological information from the patient to determine the patient's depth of anesthesia and an anesthesia administration device that delivers an amount of anesthesia to the patient. The system further includes a central monitor having a processor and configured to receive demographic information from the patient, as well as the amount of anesthetic delivered to the patient. The central monitor is further configured to determine an effect site concentration that represents a total anesthetic concentration in the patient's brain based on the amount of anesthetic. The central monitor then calculates an expected response of the patient based on the demographic information and the effect site concentration. The central monitor is further configured to determine an actual response of the patient based on the depth of anesthesia and the effect site concentration. Finally, a central monitor is configured to determine a drug sensitivity index for the patient by comparing the expected response to the actual response. For example, the depth of anesthesia monitor may be an entropy monitor or a bispectral index monitor. The expected response and the actual response may each be expressed as $EC_{50}$ values, and the drug sensitivity index may be a ratio of the expected $EC_{50}$ value and the actual $EC_{50}$ value calculated for the patient.

BRIEF DESCRIPTION OF THE DRAWINGS

The drawings illustrate the best mode presently contemplated of carrying out the disclosure. In the drawings.

DETAILED DESCRIPTION OF THE DRAWINGS

Figure 1:
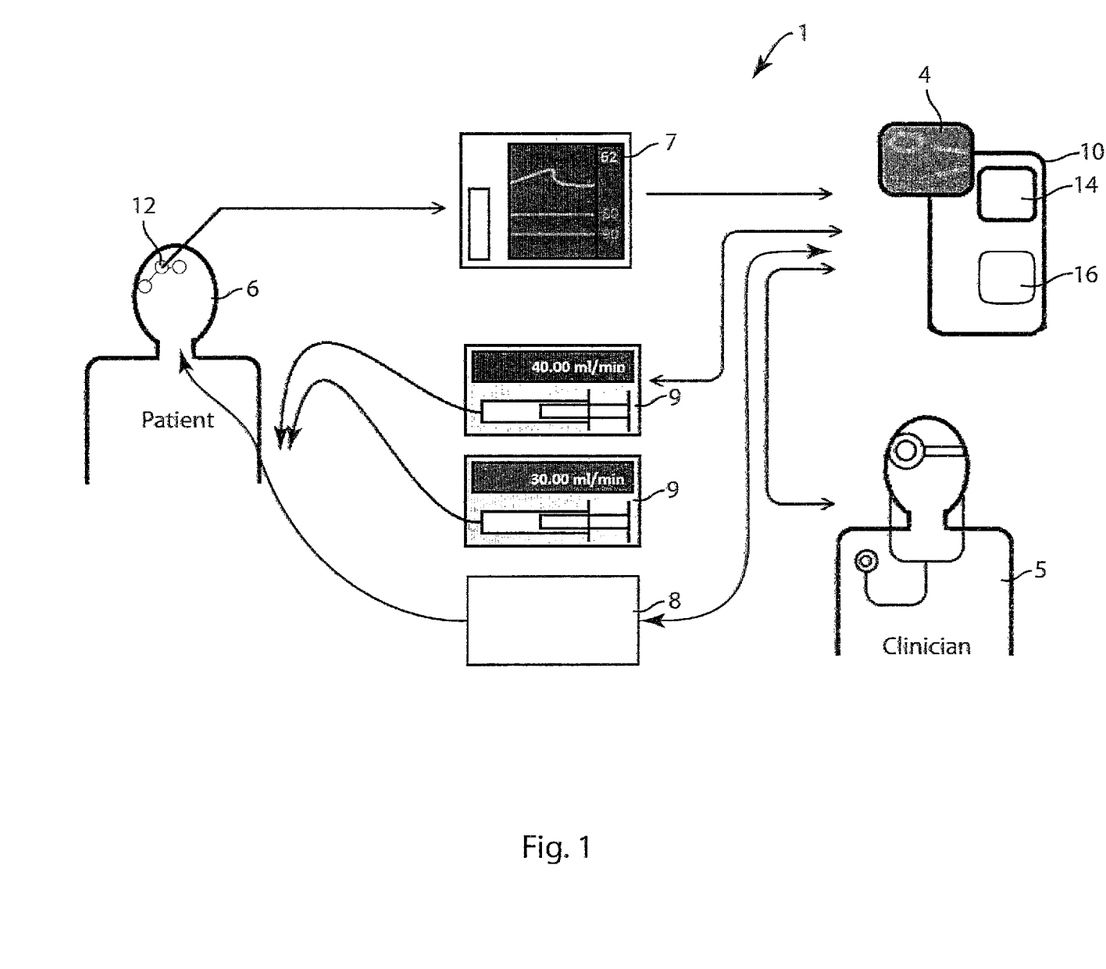
FIG. 1 depicts an exemplary system for determining patient sensitivity to anesthesia.

FIG. 1 depicts an exemplary system 1 for determining a patient's sensitivity to anesthesia and/or controlling a patient anesthesia according to the present invention. When administering anesthesia to a patient, especially when putting a patient under general anesthesia, the state of the patient 6 has to be closely monitored and controlled. The patient state is measured via a patient monitor 7, which records one or more physiological parameters from the patient using sensors 12 that connect to the patient. For example, the patient monitor may be an Electroencephalograph (EEG) device. The patient physiological information is used to determine as patient's depth of anesthesia, or sedation level. The sedation level is then used by the central anesthesia controller 10 and/or the clinician 5 as an input parameter for assessing and/or controlling anesthesia administration to the patient.

The anesthesia parameters, or dosing information, are provided to the central monitor 10 along with the data regarding the patient's depth of anesthesia. The controller 10 then employs normative population models for drug sensitivity, in conjunction with the sedation level values measured from the patient, to provide a patient-specific model that indicates the patient's sensitivity to anesthesia. In other words, the controller 10 compares the measured patient response to a defined anesthesia to the expected patient response for that defined anesthesia based on normative models in order to develop a patient-specific model that estimates the patient's response over time to that defined anesthesia. The patient-specific model, which, for example, may be expressed as a drug sensitivity index (DSI), can be used by the clinician 5 and/or the controller 10 to provide input on controlling administration of anesthetic drugs to the patient.

In one embodiment, the clinician 5 enters the infusion parameters for the pump 9 and the gas parameters for the anesthesia machine 8 at the central anesthesia controller 10. For example, the central anesthesia controller 10 may have a user interface/display 4 through which the clinician 5 inputs the anesthesia information. In another embodiment, one or both of the anesthesia parameters from the infusion pump 9 and the anesthesia machine 8 is provided automatically to the controller 10. In the embodiment of the system 1 depicted in claim 1, the anesthesia parameters are then used by a drug modeling subsystem 14 within the controller 10 to calculate the total sedation value. The entropy scaling subsystem 16 (also within the controller 10) then gathers entropy values from the patient monitor and the total sedation from the drug modeling subsystem. Then the Hill model is employed to fit the values, and the model is used to calculate a scale estimate for the individual patient.

One method for measuring anesthetic drug sensitivity includes comparing the depth of anesthesia values measured from the patient to the values calculated based on the population model to determine the individual sensitivity of the patient—e.g., a drug sensitivity index (DSI) for the patient. Specifically, the DSI may be calculated by combining the results from a PK/PD drug modeling system, such as Navigator™ Applications Suite, with the depth of anesthesia measurements from the entropy module. More specifically, the half maximal effective concentration ($EC_{50}$) value or the concentration value when the entropy is 50 ($SE_{50}$) determined from the measured patient state is compared to the same value calculated from the population model.

The $EC_{50}$ value presents the dose of a drug that will have half of the maximal effect on the patient. More specifically, population EC value for Entropy is defined as an expected synergetic effect site concentration required for a specific effect on an average patient. Here the effect is defined as a change in Entropy value from baseline (awake). $EC_{50}$ means concentration associated with half maximal effect, which is Entropy change of 50. The exact value for population $EC_{50}$ (or $EC_{50population}$) for Entropy depends on the demographic population it is derived from and also on the method. There are several ways to estimate population $EC_{50}$. It can be derived from $EC_{50}$ values of other population models by using physical models describing relationship between different responses (e.g. relation between OAA/S<2 and Entropy is well known and studied). Another way to derive population $EC_{50}$ is to use existing clinical datasets. If a dataset contains parameters required to calculate DSI value, population $EC_{50}$ can be calculated for that dataset by averaging concentration values that were required for half maximal effect. In still other embodiments, new clinical data can be collected and used to calculate DSI In one embodiment, DSI is calculated based on entropy measurements, i.e., using the $SE_{50}$ value. The $SE_{50}$ value is the effect site concentration ($C_e$) of anesthetic in the patient when the State Entropy is 50. In another embodiment, the DSI could be determined as the effect site concentration at which 50% of the patients ($C_{e50}$) had a particular measurable physiological effect compared to the concentration at which the patient demonstrated that same physiological effect. In still other embodiments, the DSI can be calculated using Bispectral Index (BIS) values, i.e., $BIS_{50}$ (the effect site concentration ($C_e$) of anesthetic in the patient when the Bispectral Index is 50), or the Hill coefficient (γ), which describes the steepness of the Hill response curve.

For example, in one embodiment the DSI may be expressed as a ratio between the population $EC_{50}$ and the patient $EC_{50}$ values. For example, DSI could be expressed as:

$$DSI = \frac{EC50_{Population}}{EC50_{Patient}}$$

Here, a DSI value of exactly 1 means that the patient's drug sensitivity is precisely aligned with the average sensitivity. Likewise, a DSI value of <1 indicates a patient drug sensitivity that is less than average, meaning that the patient requires more drugs to achieve the same level of sedation as the average individual. Conversely, a DSI value of >1 indicates a patient drug sensitivity that is greater than average, meaning that the patient requires less drugs to achieve the same level of sedation as the average individual.

The DSI can also be expressed in the opposite way, as the patient value over the population value, as in the following:

$$DSI = \frac{EC50_{Patient}}{EC50_{Population}}$$

Here, a DSI value of 1 still indicates that the patient's sensitivity is equal to the average. However, the other values are inverted, as a DSI value of <1 indicates a patient drug sensitivity that is greater than average and a DSI value of >1 indicates a patient drug sensitivity that is less than average. Again, as explained above, the $EC_{50}$ values represent the half maximal concentration values, and can take on any number of forms. $EC_{50population}$ means concentration at which, on average for the population, a half maximal effect is reached. The $EC_{50patient}$ means the concentration at which a half maximal effect is reached for the patient. Likewise, the equations could apply when using values of the entropy $SE_{50}$, gamma, $BIS_{50}$, etc.

The DSI could be expressed as a fraction of the $EC_{50}$ values (such as $EC_{50patient}/EC_{50population}$), or the DSI may be expressed as a single numerical value representing the resulting value of the comparison between the patient value and the population value. In still other embodiments, the DSI could be expressed as any other comparison or list of the expected response value (the population value) and the patient response value. In another exemplary embodiment, the DSI could be expressed as the difference between the expected response and the patient response.

Figure 2:
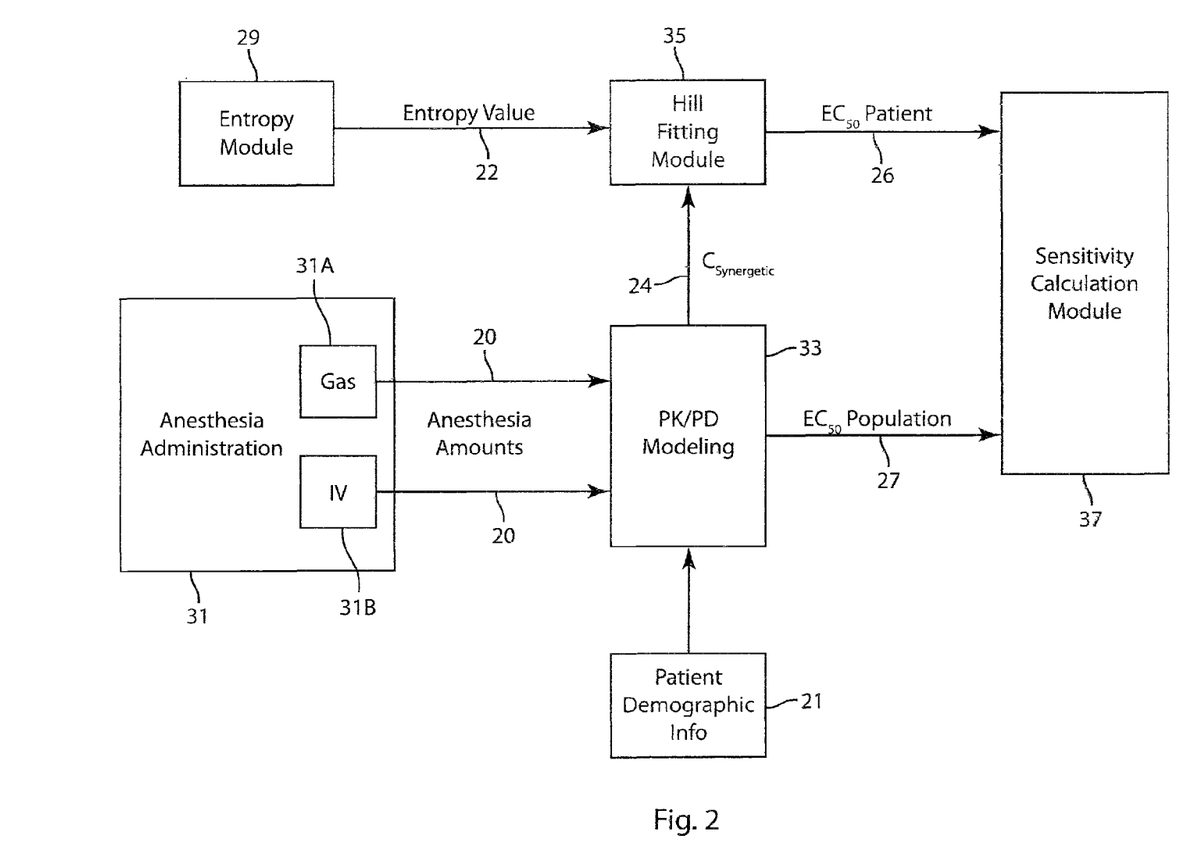
FIG. 2 depicts one embodiment of a system and method for determining patient sensitivity to anesthesia.

Referring to both FIGS. 1 and 2, determining the DSI starts by determining the amount of anesthetic 20 being delivered to the patient 6. Anesthetic may be administered as any combination of a number of different anesthetic agents, which may include anesthetic gases and/or drugs. Certain anesthetic drugs are administered intravenously by intravenous infusion, which may be done manually by a clinician or may be controlled by an infusion pump 9. Anesthetic gases are typically administered by an anesthesia machine 8 which includes a ventilator. Thus, the anesthetic amount 20 being administered to the patient includes anesthesia delivered from the infusion pump(s) 9 and/or anesthesia machines 8 for administration of volatile gas anesthetic connected to the patient 6. The anesthetic amount 20 may be entered into the central monitor 10 by the clinician 5, or the anesthetic amount 20 may be automatically read and/or controlled by the control system 10, depending on the particular arrangement of the system 1.

Typical functions of anesthesia machine 8 are ventilation of the patient (a heavily sedated patient is not capable of breathing without assistance), monitoring patient respiratory functions and administration of anesthetic gases. IV pumps 9 administer intravenous drugs to the patient, and the pumps typically operate a syringe to slowly infuse drugs to a patient intravenously at a particular dose over a specified period, e.g., ml/min. Both anesthesia machine 8 and IV pumps 9 may be individually controlled by a clinician, such as where a clinician enters a dose amount or otherwise controls the dosing directly into the one or more the anesthesia machines 8 or IV pumps 9. Alternatively, the anesthesia machines 8 and/or the IV pumps 9 may be controlled by a central monitor 10, wherein the clinician 5, such as an anesthesiologist, interacts with the central monitor 10 which in turn controls each of the individual the anesthesia administration devices.

Any combination of automatic control and manual control by a clinician 5 is possible. In one embodiment, the central monitor 10 may be integrated into the anesthesia machine 8. Commonly, anesthesia machines may include a controller providing clinical decision support and patient recordkeeping assistance. The controller, whether separate from or integrated into the anesthesia machine, may directly control one or more anesthesia administration devices, such as the infusion pump(s) 9 and the anesthesia machine(s) 8. This central control may be automatic or it may be in response to dosing information entered by the clinician. Alternatively, the central monitor 10 may simply provide information to the clinician 5 that the clinician can use to manually control one or more of the anesthesia administration devices.

FIG. 2 discloses an exemplary system and method for determining anesthetic drug sensitivity. Each step of the method and/or element of the system is described in more detail herein below.

Anesthesia Administration

As generally described above, Anesthesia administration 31 may be accomplished using a number of devices alone or in combination. In general, drugs associated with general anesthesia can be divided to three categories: hypnotics, analgesics and relaxants. Hypnotics are used to induce unconsciousness and amnesia. A common intravenous hypnotic is propofol. Common inhaled anesthetics with hypnotic effects include desurane, isourane and sevourane. Analgesics are used for antinociception, that is, to remove pain. There are several analgesics that can be used during anesthesia. Some common ones are opioids alfentanil, fentanyl, remifentanil and sufentanil. Relaxants are used to achieve immobility of the patient during operation by suppressing muscle activity.

Referring to both FIGS. 1 and 2, gas anesthetics, or inhaled anesthetics, may be administered by an anesthesia machine 8, such as that described above. A typical gas module 31A measures multiple parameters, including flow pressure and concentration of inspired and expired gases. When administering inhaled anesthetics, it is important to measure how the anesthetic is absorbed by the patient. This can be done by a gas module 31A, such as an anesthesia machine 8 that includes a gas analyzer, and the anesthetic amounts 20 determined or measured by the gas module 31A are then transferred to a processor, such as a central monitor 10. The gas analyzer has a sample line connected to the breathing circuit, and it analyzes the inhaled and exhaled gases to determine how much of the anesthesia gas is absorbed by the patient. The gas analyzer line, itself, may be connected to the anesthesia machine 8 or the central monitor 10, and thus the absorption may be determined at either physical location.

Infusion pumps 9 are used to administer intravenous (IV) drugs to the patient, such as propofol and opioids (e.g., remifentanil and alfentanil). These pumps are often digitally controlled and the infusion rate can be precisely determined in an infusion module 31B. The infusion rate comprises anesthetic amount information 20 that is transferred to a central processor, such as a central monitor 10. The infusion module 31B may be integrated into or connected to a data gathering device, such as a medical PC, that allows an exact amount of administered drug to be automatically recorded. Alternatively or additionally, pumps may allow remote control, such as by a central monitor 10 or a remote control device operated by a clinician 5. A pump can be controlled manually by setting infusion rate or by selecting a bolus amount. More automated control can be achieved by using Target Controlled Infusion (TCI) pump that allows anesthetist to set target concentration instead of manually adjusting infusion rate. This makes fast adjustments easier and thus increases safety and decreases workload. TCI mode is preferred to manual control for the pumps that support it. There are two kinds of TCI modes: blood targeted and effect site targeted. These differ by the internal drug model that the pump, or the controller for the pump, uses to calculate the rate.

Monitoring Sedation Level

Multiple methods of sedation monitoring are available and may be employed in the present system and method. One common sedation meter is Bispectral Index (BIS), which typically employs a three electrode sensor put on the forehead of the patient. BIS is a simple scale of 100 to 0 that is supposed to directly tell the state of the patient, 100 meaning fully conscious patient and 0 meaning completely sedated patient. Other EEG based measurement systems are available and have been utilized as sedation monitoring tools, such as Auditory Evoked Potentials (AEP), Index of Consciousness (IoC), Patient State Analyzer (PSA) and Spectral Entropy (SE). However, BIS, as well as these other processed EEG embodiments, only provide an approximation of the patient's sedation level and cannot directly indicate the level of patient awareness.

In the embodiment depicted in FIGS. 1 and 2, entropy is used as the measurement for measuring the patient sedation level. An entropy sensor 12 is on the forehead of the patient 6. The patient monitor 7 may have an entropy module 29 and the sensor is connected to the module by a cable. The entropy module 29 determines entropy based on the patient data gathered from the sensor 12. The entropy module 29 may be a stand-alone patient monitor 7, integrated into with another patient monitor, or it may be integrated into the central monitor 10. The entropy module 29, such as the patient monitor 7, may have a display that shows current entropy values and/or a trend graph of entropy values over time.

Entropy has two main parameters, State Entropy (SE) and Response Entropy (RE), each of which may be determined in an entropy module 29. SE and RE have different weighting on individual frequency channels so that RE reacts more on EMG than SE. This makes it possible to detect patient response to stimulation by following the difference between RE and SE. Further, since SE focuses on frequency channels that are for the most part outside of the EMG frequency range, SE is not significantly affected by relaxants or external stimulus. RE utilizes a scale of 100 to 0, and SE utilizes a 91 to 0 scale. In typical sedation, the SE or BIS value is kept in the middle of the range, between values 40 and 60. Entropy values much below 40 indicate burst suppression, meaning that the cortex of the brain starts to shut down for short periods of time. Burst suppression by itself is not a risk to the patient, but it can indicate unnecessarily deep anesthesia. The entropy module may also measure Burst Suppression Rate (BSR), which has range of 0 to 100 percent. However, in typical operation where SE is within normal range, BSR may not be of much interest as it stays close to zero.

In another embodiment, the entropy module 31A may be replaced by a BIS module, which is similar to and entropy module 31A in that it typically employs a simple, three lead sensor to measure the signal of a single EEG channel. The main difference between entropy and BIS is that BIS uses several different models depending on phase of anesthesia, whereas and entropy module uses only one model. Further, in BIS the electromyographical (EMG) component of the signal is filtered out, whereas EMG is considered as part of the entropy measurement. In still other embodiments, the entropy module 31A may be any module for determining patient sedation level.

Drug Models and Correlating Patient Sedation to Drug Concentration

With inhaled agents it is possible to estimate blood concentration by analyzing exhaled gases. However, currently there is no equivalent commercial point of care measurement system for intravenous anesthetics. This means that excluding research setups, it is not possible to directly measure concentration of intravenous drugs in a patient, such as during surgery. Thus, drug models are currently used to determine blood concentration; and only way to estimate the correct dosage is to use drug models.

The present method can employ any drug modeling technique to determine concentration. Currently available drug modeling techniques provide drug concentration information on a demographic population scale. When population model parameters are researched, it is common practice to calculate $EC_{50}$ values for all patients in the dataset. The $EC_{50}$ values may then be averaged to get population averages—i.e. the $EC_{50 population}$ 27. The patient's demographic information 21 may be defined in any number of ways that are clinically significant for predicting patient sensitivity to anesthesia. For example, the population demographic applicable for a patient may be defined based on the patient's age, height, weight, and gender.

One common population model is the PK/PD model, which can be used during a surgical operation to estimate patient level of consciousness. A PK/PD model means pharmacokinetic/pharmacodynamic model, or a pharmacokinetic model that is shown relative to the corresponding pharmacodynamics model (PK normalized by PD). In a PK/PD model, the effect site is modeled as connect directly to the central compartment. More specifically, the effect site concentration follows the central compartment with a delay.

The PK/PD module 33 applies the PK/PD model to anesthesia amount data to determine the expected, or estimated, drug concentration levels in the patient based on the patient's demographic information 21. The patient demographic information 21 may be entered into the system by the clinician 5, such as at the monitor 4 of the central monitor 10. Alternatively, the central monitor 10 may automatically obtain the needed patient demographic information 21 from a database of patient information. For example, the central monitor 10 may be connected to the computer network of a healthcare facility, and thus may obtain the demographic information 21 over the network from a database of patient information housed somewhere on the network.

Pharmacokinetics attempts to answer the question of what happens to the drug after it enters the body. Pharmacokinetic (PK) models describe how the drug is dispersed in to the body and what the drug concentration is in a particular area of interest at given time. A typical PK model produces blood concentrations from amounts of drug administered. Alternatively, in target controlled infusion a PK model can be used to calculate blood concentrations from given target concentrations. Most PK models for anesthetics are based on the assumption that the human body consists of multiple compartments. Here a compartment is an abstract entity that presents collection of similarly behaving tissues. The compartment is defined by volume and by the diffusion speed coefficient. Each compartment has some drug concentration and the drug diffuses from the higher concentration to the lower. The central compartment of these models correspond to the circulatory system i.e. blood. In a two compartment model these the tissues are modeled as a single peripheral compartment. In a three compartment model the other tissues are modeled as the fast and the slow peripheral compartment, according to the diffusion speeds. The three compartment model is often used for modeling propofol and it gives useful results. The three compartment model can be expressed as a system of equations:

$$\dot{q}_1 = q_2 k_{21} + q_3 k_{31} - q_1(k_{10} + k_{12} + k_{13}) + u_1;$$

$$\dot{q}_2 = q_1 k_{12} - q_2 k_{21};$$

$$\dot{q}_3 = q_1 k_{13} - q_3 k_{31};$$

where $q_n$ is the concentration in the compartment n and $\dot{q}_n$ is the time derivative of the concentration. $k_{nm}$ is the diffusion speed coefficient between compartments n and m. Term $u_1$ is the amount of drug introduced to the system and $k_{10}$ is the elimination speed coefficient.

The PK model is used to compute the blood concentration. Then PD model is used to compute the effect site concentration ($C_e$) of the drug by delaying the values of blood concentration according to effect site diffusion speed coefficient. The effect site concentration ($C_e$) is then normalized (or scaled) to the PD model, the $EC_{50}$ for the demographic population ($EC_{50population}$) 27. The PK/PD model can be displayed as a plot of $C_e(t)/EC_{50}$ over time, where $C_e(t)$ is the effect site concentration of the drug for time t, and $EC_{50}$ is the effect site concentration at which 50% of the maximal drug effect is experienced.

As described, the Hill equation defines a projection from concentration to effect. It is generally written so that it defines the clinical effect (E) as a function of effect site concentration ($C_e$):

$$E = E_{min} + (E_{max} - E_{min}) \frac{C_e^\gamma}{EC_{50}^\gamma + C_e^\gamma}$$

The parameters of function are the smallest possible effect ($E_{min}$), the largest possible effect ($E_{max}$), half maximal effective concentration ($EC_{50}$), and the Hill coefficient ($\gamma$) that defines the steepness of the Hill curve. E can represent any measure of effect, though the equation may undergo some modification depending on the effect measurement. For example, in one embodiment the Hill equation can be used to model the relation between state entropy (SE) and $C_e$, which may be depicted as follows:

$$SE = SE_{max} - (SE_{max} - SE_{min}) \frac{C_e^\gamma}{EC_{50}^\gamma + C_e^\gamma}$$

Here the factor is negative because increasing drug concentration causes Entropy to decrease. Further, as explained in more detail below, the Hill equation can also be fitted to gathered data, such as state entropy and effect site concentration values.

Figure 3A:
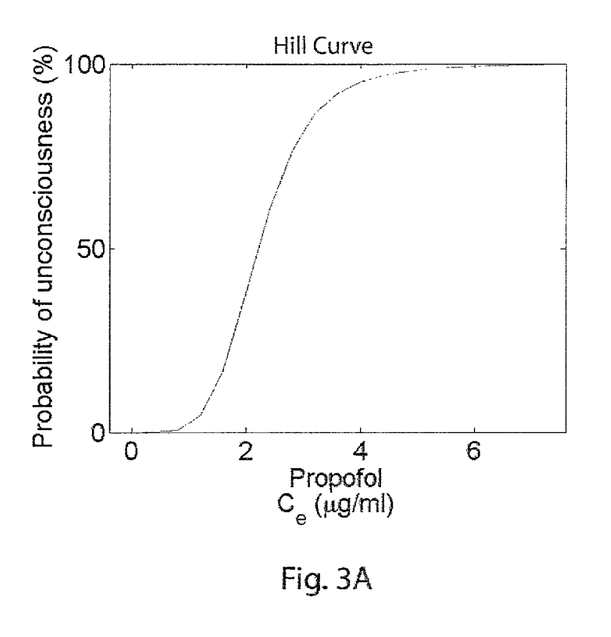
FIGS. 3A and 3B depict exemplary Hill Curves comparing anesthetic dosing to the probability of unconsciousness.
Figure 3B:
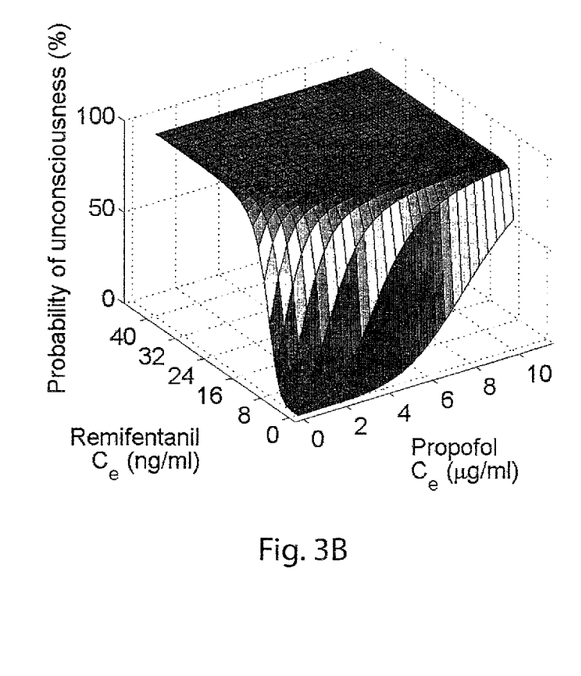

As seen in FIGS. 3A and 3B, the Hill curve, which presents the probability of unconsciousness (in percent) with respect to the effect site concentration ($C_e$) of a particular anesthetic or combination of anesthetics, has a sigmoid shape. This means that very small doses are not enough to cause noticeable response. If the dose is increased above certain point the effect increases rapidly to almost maximum. Saturation is reached and increasing dose further causes little change on the response. FIG. 3B illustrates an exemplary Hill curve for a combination of drugs. A Hill equation model can provide information regarding the synergistic effect of multiple drugs administered simultaneously. An interaction model is used for calculating synergetic effect of multiple drugs. There are two different kinds of synergy between drugs, PK and PD. PD synergy is more significant of these two. When calculating synergetic effect, typically only PD synergy is taken into consideration. The drugs with the same mechanism have typically no synergetic effects. This means that when administering several opioids, the normalized concentrations can be simply added together. On the other hand, drugs with synergistic effects have compounding effects, and thus the resulting effect will be different than, usually greater than, the sum of each of the normalized concentrations. For example, the propofol and opioids have a strong PD synergy. The same is true for gas agents and opioids. This means that, for example, when administering both propofol and remifentanil the clinical effect is much larger than with either of the drugs administered alone. Moreover the effect is greater than the sum of individual effects.

A graded response curve may be used for a gradually changing response such as entropy. However, sometimes it is useful to predict the probability of a clinical event, such as loss of consciousness. Such an event-centered model does not change gradually, but instead has either no response or full response. Systems with this kind of quantal response are best modeled with a quantal response curve that defines the relation between the dose and the probability of the response.

Synergy models are often described in the terms of Response Surface Method (RSM), such as that shown in FIG. 3B where effects of the two synergetic drugs (remifentanil and propofol) are presented as a three dimensional surface graph. For example, synergistic effect can be calculated as a product of a synergy coefficient and the individual effects of each drug. One exemplary embodiment The synergetic effect site concentration ($C_{synergetic}$) 24 for propofol and remifentanil may be calculated by the following:

$$C_{synergetic} = EC_{50p}\left(\frac{C_{prop}}{EC_{50p}} + \frac{C_{remi}}{EC_{50r}} + \alpha\frac{C_{prop}}{EC_{50p}}\frac{C_{remi}}{EC_{50r}}\right)$$

where $EC_{50p}$ is equal to the $EC_{50}$ for propofol, EC50r is equal to is the $EC_{50}$ for remifentanil, $C_{remi}$ is the effect site concentration of remifentanil, $C_{prop}$ is the effect site concentration of propofol, and alpha is the synergy coefficient between propofol and remifentanil. Further information regarding calculation of the synergy coefficient is described at, for example, Johnson, K. B., Syroid, N. D., Gupta, D. K., Manyam, S., Egan, T. D., Huntington, J., White, J. L., Tyler, D., and Westenskow, D. K. "Validation of remifentanil propofol response surfaces for sedation, surrogates of surgical stimulus, and laryngoscopy in patients undergoing surgery." *Anesthesia and Analgesia* 106, 2 (February 2008).

Comparing Sedation Level to Normative Models to Develop a Sensitivity Measurement and Sedation Model for the Patient Referring again to the embodiment of FIG. 2, the Hill model can be used to correlate the entropy values 22 measured from the patient to the drug concentrations, such as the synergetic effect site concentration values ($C_{synergetic}$) 24 determined by the PK/PD module 33. That correlation is performed at the Hill fitting module 35, which determines the patient specific correlation value, such as the $EC_{50patient}$ value 26 described above. That patient-specific correlation is passed to the sensitivity calculation module 37, which calculates the DSI based on the comparison between the patient value and the expected value. For example, in the embodiment of FIG. 2, the sensitivity calculation module 37 calculates the DSI as the ratio between the $EC_{50population}$ and the $EC_{50patient}$.

Other correlation methods and modules can be used to calculate the patient-specific DSI. As described above, the DSI is a comparison between the measured response and the expected response. Thus, that comparison may be made based on any number of parameters that are affected by anesthetics, or measurements of sedation level. For example, the Hill coefficient (gamma or γ) may be employed instead of the $EC_{50}$ value. Entropy response to anesthetics is non-linear so there is actually two parameters to response curve: $EC_{50}$ and gamma. Gamma describes the steepness of the response curve, and thus can be interpreted as sensitivity in a mathematical sense. These parameters both have a positive correlation with concentration, so either can be used for calculating sensitivity. Using $EC_{50}$ may be more logical, or intuitive, from the clinical point of view. However, gamma may also be used with equal effectiveness. Likewise, any numerical index derived from EEG such as Narcotrend index, Bispectral Index (BIS), Evoked Potentials (AEP), Index of Consciousness (IoC), and Patient State Analyzer (PSA) could also be employed to determine a DSI for the patient.

Implementing the Patient Sensitivity Measurement to Monitor and Control Anesthesia The DSI may be implemented to create a patient-specific model of the patient's sedation level for a given course of anesthesia. Namely, the results of the population model(s) for the patient's demographic may be normalized to the depth of anesthesia values obtained from the patient monitor. Thereby, the patient-specific model may be used to predict, probabilistically, when the patient will return to consciousness. Likewise, the model can be implemented to predict the probability of a clinical event such as loss of consciousness. Moreover, the model may be used to determine what course or dose of anesthesia will achieve optimal results based on the anesthetic goal, and thereby guide clinicians in avoiding under dosing or overdosing the patient.

The patient drug sensitivity index and/or other predictive information about the patient's sedation level may be displayed to the clinician 5, such as on the display 4 of the central monitor 10. The display 4 of the central monitor 10 may also act as a user input device and may provide a user interface that may allow the clinician to view various aspects or implementations of the DSI values. For example, as demonstrated in FIG. 4, the user interface can be implemented to display drug modeling results on the entropy scale.

Figure 4:
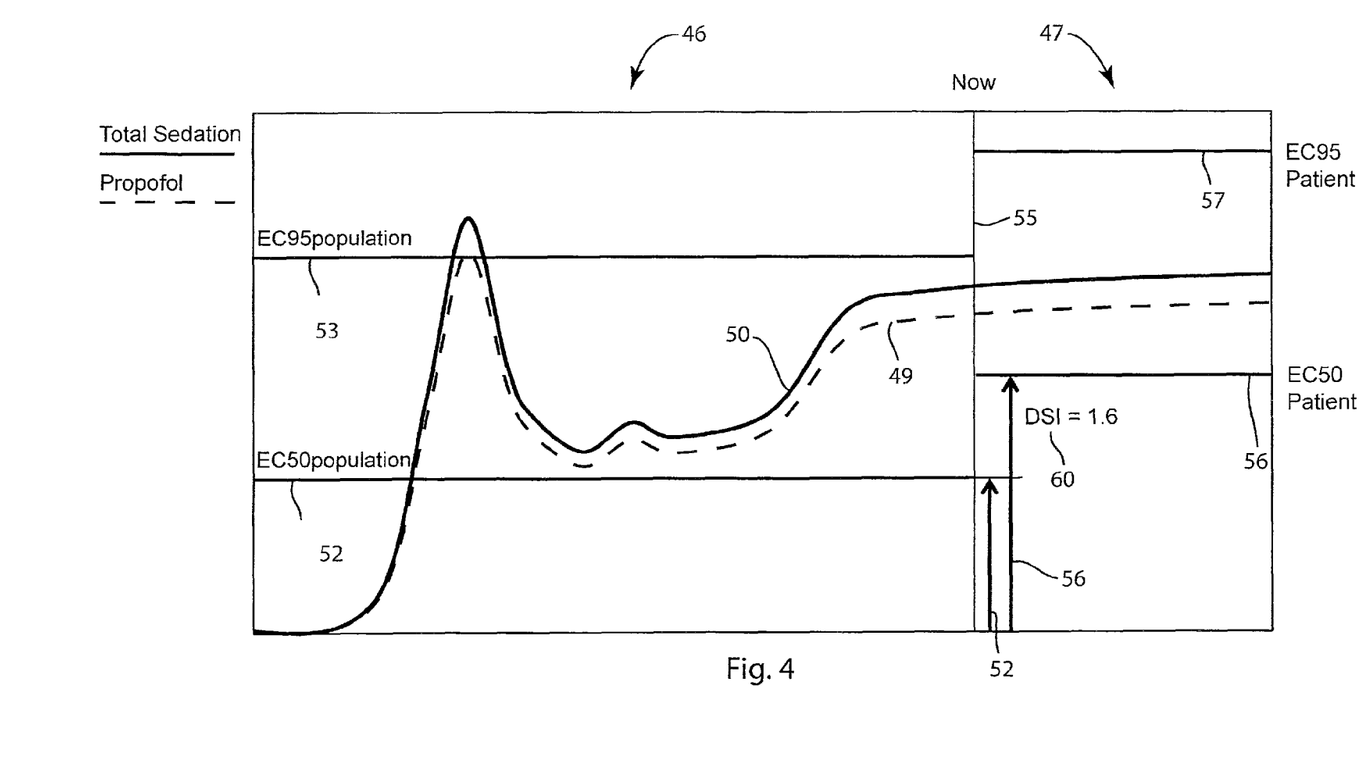
FIG. 4 depicts a comparison between the modeled effect site concentration and the patient-specific effect site concentration.

FIG. 4 demonstrates the past modeled effect site concentrations shown on the population scale 46 next to the predicted effect site concentrations shown on the patient scale 47. The population scale 46 portion of the graph and the patient scale portion of the graph are separated by the "now" line 55, which represents the current time of the graph. The total sedation line 50 shows the total effect site concentration of all of the combined administered anesthetic, whereas the propofol line 49 shows the isolated portion of the effect site concentration of just propofol. On the population side of the graph, the $EC_{50population}$ 52 and $EC_{95population}$ 53 are shown, which are the average $EC_{50}$ and $EC_{95}$ values calculated for the demographic population. On the patient side of the graph, the $EC_{50patient}$ 56 and $EC_{95patient}$ 57 values are displayed, which are the patient-specific calculated values. The DSI is illustrated by comparing the $EC_{50population}$ 52 to the $EC_{50patient}$ 56, which are illustrated by both the respective $EC_{50}$ lines and the arrows pointing thereto. In the exemplary graph of FIG. 4, the exemplary patient's DSI 60 equals 1.6, which is calculated in this embodiment as the $EC_{50patient}$ divided by the $EC_{50population}$.

In some embodiments the central monitor 10 may be configured to provide an alert if the DSI is below a predetermined minimum level or above a predetermined maximum level. In other words, an alert may be provided if the patient is especially sensitive or especially insensitive to a given course of anesthesia. Similarly, the central monitor 10 may provide an alert to the clinician if the level of anesthesia being provided to the patient is insufficient to maintain at least a predefined sedation level, or depth of anesthesia. For example, the central monitor 10 may alert the clinician if the anesthetic dose is insufficient to keep the patient from regaining consciousness for at least a predefined period of time.

The DSI may be utilized to provide information for making decisions about a particular course of anesthesia for a patient. For example, a clinician may rely in part on the DSI, or on some implementation thereof, when determining what dose(s) of anesthesia to administer to the patient. Thus, the DSI can be implemented to predict the future SE values for a patient at a given course of anesthesia, and then the clinician can operate the anesthesia devices accordingly. In another embodiment, the DSI may be utilized as an input parameter to an anesthesia controller, such as in a closed loop controller that automatically controls the anesthesia devices to adjust the anesthesia administration to achieve a particular effect, such as a particular sedation level. In such an embodiment, the controller may implement the patient's DSI to determine an appropriate course of anesthesia for achieving a particular sedation level at a particular time for that patient. The controller may then utilize the depth of anesthesia information from the patient monitor as feedback in the control algorithm, upon which it can automatically fine time the DSI model and/or adjust the dosage so that the desired sedation level is achieved.

In one exemplary embodiment of the patient sensitivity measurement, DSI is calculated from a collection of time-stamped SE values collected at 10 second intervals over 10 minutes and a collection of time-stamped synergetic effect site concentrations that have been calculated from the recorded drug administrations. The calculation is performed according to the following exemplary steps. A Hill equation is defined, such as described above, with constant maximum ($SE_{max}$) and minimum ($SE_{min}$) values and variable gamma and EC50. $SE_{min}$ and $SE_{max}$ may be selected to be constant 0 and 91. An exemplary embodiment of an implementation of the Hill equation is further described in Hahn, J.-O., Khosravi, S., Dumont, G. A., and Ansermino, J. M. "Two-stage vs. mixed-effect approach to pharmacodynamic modeling of propofol in children using state entropy." *Pediatric Anaethesia* 21, 6 (2011): 691-698. The exemplary algorithm described therein minimizes the EC50 and gamma parameters of the Hill equation. The Hill equation is difficult to fit analytically so a numerical method may be used to find the parameters. The approach may be to define an error function and minimize it using general numerical methods. For example, the constraints for the minimized may be selected as selected as $0.1\ C_{max} \ldots 0.9\ C_{max}$ for $EC_{50}$ and $e^{-1} \ldots e^{1}$ for gamma.

An error function is then defined as the MSE between SE and SE approximated with the Hill equation. This means that for each SE value an approximation is calculated from Ce. The range of gamma and EC50 form an error surface that is minimized by using a general numerical method, such as the Nelder-Mead Simplex or the Levenberg-Marquardt algorithm. The error function may be defined as the mean squared error (MSE) between the estimated ($\widehat{SE}_t$) and measured ($SE_t$) values:

$$MSE_{SE} = \frac{1}{N}\sum_{t=1}^{N}(\hat{SE}_t - SE_t)^2$$

Further, a weight parameter may be added to ignore some of the values when fitting. Thus, the error function of the fitting algorithm may be:

$$MSE_{SE} = \frac{1}{N}\sum_{t=1}^{N}weight_t(\hat{SE}_t - SE_t)^2$$

where $weight_t$ is the weight of the sample at time t. With the weight parameter added it is possible to drop values that contain no useful information.

This principle may also be applied to missing values in the State Entropy and for filtering out the values with high difference between RE and SE. For example, a MATLAB® prototype may be employed that uses a modified simplex algorithm to find best values and to minimize the target function. In practice, this means that it starts from an estimate that is defined as a set of parameters for the target function and then updates the estimate at every iteration. The update rule selects the next estimate so that the target function value is always smaller than with the current estimate. If target function has only one minimum, this algorithm will converge to that eventually. However, if the function used is not constrained, such as the MATLAB® function (fminsearch), constraints may to be added to error function. For example, values outside the constraints may be defined to have an infinite penalty.

Figure 5:
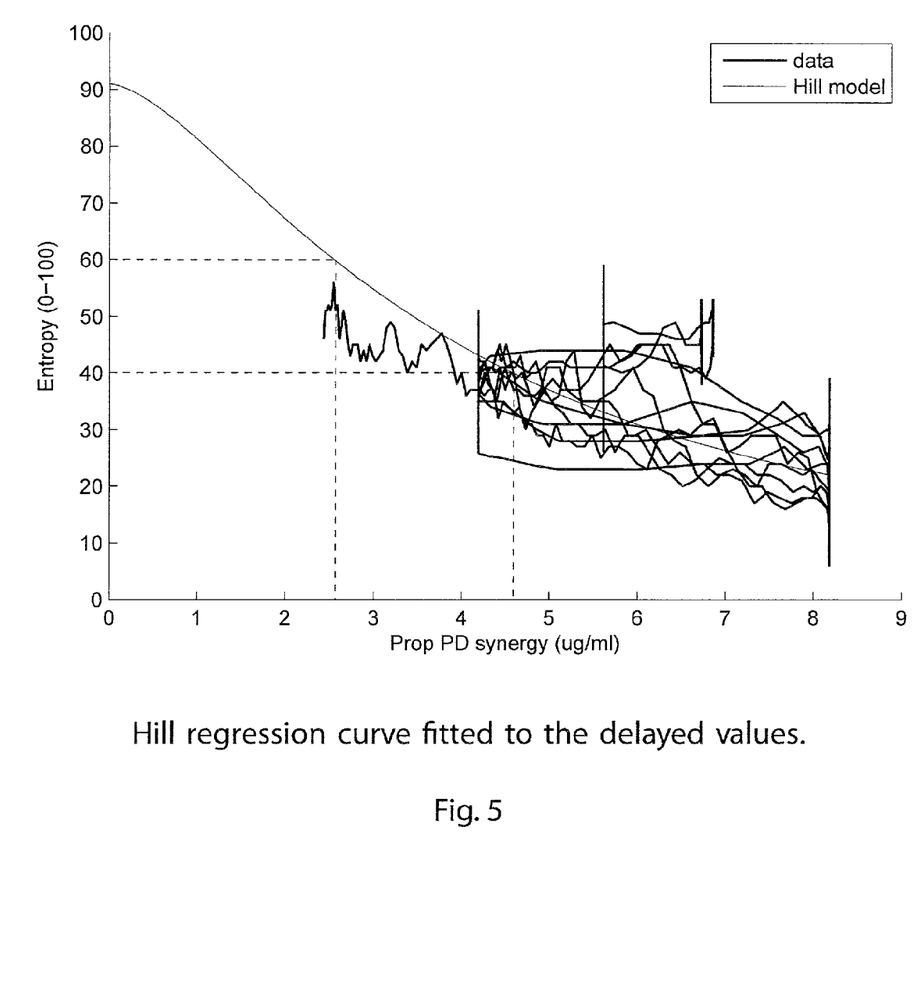
FIG. 5 depicts an exemplary regression curve fitted to a data set for determining Hill values.

After finding the parameters for the Hill equation, a regression curve may be plotted over the data points. In FIG. 5 an exemplary regression curve is seen with vertical lines denoting Ce values that correspond to SE values of 40 and 60. Minimizing the error function yields the values to gamma and EC50 parameters. To take account possible delay between SE and Ce, this process may be repeated several times for different delays (e.g., 0 to 3 min). With each delay iteration, EC50 and MSE may be recorded and the EC50 value that has lowest associated MSE selected. As is described above, calculating the ratio of this $EC_{50}$ value and $EC_{50}$ of population model results in DSI.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of monitoring a patient under anesthesia, the method comprising:
    obtaining patient demographic information of a patient;
    obtaining amount of anesthetic information, wherein the amount of anesthetic information includes each drug administered to the patient and the dose amount thereof;
    estimating an effect site concentration based on the anesthetic information using a processor, wherein the effect site concentration represents a total anesthetic concentration in the patient's brain;
    determining an expected response of the patient using a processor based on the demographic information and the effect site concentration;
    recording physiological data from sensors mounted to the patient;
    determining a depth of anesthesia for the patient based on the physiological data;
    determining an actual response of the patient based on the depth of anesthesia and the effect site concentration; and
    determining a drug sensitivity index for the patient by comparing the expected response to the actual response.

2. The method of claim 1, wherein the physiological information recorded from the patient is EEG data.

3. The method of claim 2, wherein the depth of anesthesia is an entropy value.

4. The method of claim 1, wherein the effect site concentration is determined using a drug modeling method.

5. The method of claim 4, wherein the drug modeling method is a pharmacokinetic model normalized to a corresponding pharmacodynamic model (a PK/PD model).

6. The method of claim 1, wherein the expected response and the actual response are each expressed as half-maximal effective concentration ($EC_{50}$) values.

7. The method of claim 6, wherein the drug sensitivity index is equal to an expected $EC_{50}$ value divided by a patient $EC_{50}$ value, wherein the expected $EC_{50}$ value is the average $EC_{50}$ for the patient's demographic population and the patient $EC_{50}$ value is calculated based on the depth of anesthesia for the patient and the effect site concentration.

8. The method of claim 7, wherein the patient $EC_{50}$ value is calculated by fitting the Hill equation to a time plot of the depth of anesthesia values and effect site concentration values for the patient.

9. The method of claim 1, wherein the expected response represents an average response of subjects sharing the same demographic information as the patient.

10. The method of claim 1, wherein the drug sensitivity index equals 1 when the expected response equals the actual response.

11. The method of claim 1, wherein the expected response and the actual response are each expressed as effect site concentration when the entropy is 50 ($SE_{50}$) values.

12. The method of claim 1, wherein the expected response and the actual response are expressed as Hill coefficient values.

13. The method of claim 1, wherein the depth of anesthesia is a Bispectral Index value.

14. The method of claim 1, wherein the drug sensitivity index is displayed to a clinician.

15. A monitoring system for monitoring a patient under anesthesia, the monitoring system comprising:
   a depth of anesthesia monitor that records physiological information from the patient to determine the patient's depth of anesthesia;
   an anesthesia administration device that delivers an amount of anesthetic to the patient;
   a central monitor having a processor, wherein the central monitor is configured to:
      receive demographic information of the patient;
      receive the amount of anesthetic delivered to the patient;
      determine an effect site concentration that represents a total anesthetic concentration in the patient's brain based on the amount of anesthetic delivered to the patient;
      determine an expected response of the patient based on the demographic information and the effect site concentration;
      determine an actual response of the patient based on the depth of anesthesia and the effect site concentration; and
      determine a drug sensitivity index for the patient by comparing the expected response to the actual response.

16. The system of claim 15, wherein the depth of anesthesia monitor is an entropy monitor and wherein the expected response and the actual response are each expressed as an effect site concentration value when entropy is 50 ($SE_{50}$).

17. The system of claim 15, wherein the depth of anesthesia monitor is a Bispectral Index monitor and wherein the expected response and the actual response are each expressed as an effect site concentration value when Bispectral Index is 50 ($BIS_{50}$).

18. The system of claim 15, wherein the central monitor has a display and is configured to display the drug sensitivity index.

19. The system of claim 15, wherein the anesthesia administration device automatically communicates the amount of anesthesia to the central monitor, and wherein the central monitor automatically controls the anesthesia administration device based on the drug sensitivity index.

20. The system of claim 15, wherein the central monitor utilizes the drug sensitivity index to provide a sedation level prediction for the patient, wherein the sedation level prediction is a prediction of the patient's sedation level at a future time for an amount of anesthesia.

* * * * *